(12) United States Patent
Gadsby

(10) Patent No.: US 6,600,957 B2
(45) Date of Patent: Jul. 29, 2003

(54) HIGH-ENERGY DISPOSABLE MEDICAL STIMULATION ELECTRODE

(75) Inventor: Peter D. Gadsby, East Longmeadow, MA (US)

(73) Assignee: The Ludlow Company LP, Chicopee, MA (US)

(*) Notice: Subject to any disclaimer, the term of this patent is extended or adjusted under 35 U.S.C. 154(b) by 89 days.

(21) Appl. No.: 09/893,855

(22) Filed: Jun. 28, 2001

(65) Prior Publication Data
US 2003/0004558 A1 Jan. 2, 2003

(51) Int. Cl.⁷ .................................................. A61N 1/04
(52) U.S. Cl. ........................................ 607/142; 607/152
(58) Field of Search ................................. 607/142, 152

(56) References Cited

U.S. PATENT DOCUMENTS

| | | | |
|---|---|---|---|
| 1,989,282 A | 1/1935 | Kimble et al. | 607/152 |
| 4,257,424 A | 3/1981 | Cartmell | 600/385 |
| 4,365,634 A | 12/1982 | Bare et al. | 600/391 |
| 4,426,461 A | 1/1984 | Smith | 521/116 |
| 4,522,211 A | 6/1985 | Bare et al. | 600/392 |
| 4,643,193 A | 2/1987 | DeMarzo | 600/392 |
| 4,736,752 A | 4/1988 | Munck et al. | 607/152 |
| 4,852,571 A | 8/1989 | Gadsby et al. | 600/396 |
| 4,979,517 A | 12/1990 | Grossman et al. | 607/153 |
| 5,063,932 A | 11/1991 | Dahl et al. | 600/374 |
| 5,111,812 A | 5/1992 | Swanson et al. | 607/2 |
| 5,143,089 A | 9/1992 | Alt | 128/784 |
| 5,265,579 A | 11/1993 | Ferrari | 128/640 |
| 5,337,748 A | 8/1994 | McAdams et al. | 607/152 |
| 5,352,315 A | 10/1994 | Carrier et al. | 156/267 |
| 5,411,527 A | 5/1995 | Alt | 607/5 |
| 5,431,166 A | 7/1995 | Macur | 607/152 |
| 5,450,845 A | 9/1995 | Axelgaard | 607/152 |
| 5,465,715 A | 11/1995 | Lyons | 128/640 |
| 5,571,165 A | 11/1996 | Ferrari | 607/142 |
| 5,733,324 A | 3/1998 | Ferrari | 607/152 |
| 5,785,040 A | 7/1998 | Axelgaard | 607/149 |
| 5,824,033 A | 10/1998 | Ferrari | 607/142 |
| 5,843,155 A | 12/1998 | Axelgaard | 607/152 |
| 5,865,740 A | 2/1999 | Kelly et al. | 600/382 |
| 5,904,712 A | 5/1999 | Axelgaard | 607/148 |
| 5,928,571 A | 7/1999 | Chan | 252/514 |
| 6,038,485 A | 3/2000 | Axelgaard | 607/148 |
| 6,152,955 A | 11/2000 | KenKnight et al. | 607/129 |
| 6,356,779 B1 * | 3/2002 | Katzenmaier et al. | 600/391 |

* cited by examiner

*Primary Examiner*—Carl Layno
(74) *Attorney, Agent, or Firm*—RatnerPrestia

(57) ABSTRACT

A disposable medical electrode for delivering high-energy defibrillation or pacing stimulation and having energy dispersion characteristics. A fanned wire contacts the top of an electrode member for delivering energy to and transmitting energy from the electrode. A hydrogel is disposed on the bottom of the electrode member and an electrically conductive metal/metal chloride ink coating underlies the hydrogel. The ink coating has (a) a center with a first amount of ink, (b) an inner edge defining the terminus of the center and a step at which the ink content of the ink coating drops from the first amount of ink to a lesser second amount of ink, (c) an outer edge defining the terminus of the ink, and (d) a predetermined gradient disposed between the inner edge at which the ink coating has the second amount of ink and the outer edge at which the ink is substantially absent.

33 Claims, 8 Drawing Sheets

HIGH-ENERGY DISPOSABLE MEDICAL STIMULATION ELECTRODE

TECHNICAL FIELD

The present invention relates generally to medical electrodes and, more particularly, to disposable medical electrodes intended for high-energy stimulation (i.e., defibrillation, pacing, and the like) with energy dispersion characteristics.

BACKGROUND OF THE INVENTION

Medical electrodes provide an electrical interface between a patient and monitoring equipment (e.g., an electrocardiograph device) or between a patient and stimulating equipment (e.g., interferential and iontophoresis devices). A specific type of stimulating electrode, used to provide an electrical interface between a patient and defibrillation equipment, must be capable of conducting the high-energy level required for defibrillation. The present invention focuses on high-energy defibrillation and pacing electrodes. The general characteristics of, and distinctions among, monitoring electrodes, general stimulating electrodes, and defibrillation electrodes are outlined below.

A. Monitoring Electrodes

Medical monitoring electrode systems help to obtain desired physiologic responses for the assessment or treatment of diseases and injuries in humans. Monitoring electrodes are used to sense electrical signals, which are then transmitted to electrocardiograph (EKG), electroencephalograph (EEG), and electromyograph (EMG) devices. In general, monitoring electrodes for EKG, EEG, and EMG devices are small, for example on the order of a few square centimeters, because a relatively small contact area with a skin surface is sufficient for reception of electrical signals. Monitoring electrodes need only carry very low electrical signals: on the order of milliamps. In general, monitoring electrodes are not capable of conducting and distributing the high levels of energy required in transcutaneous stimulation and defibrillation electrodes.

Various x-ray transmissive monitoring electrodes have been made to facilitate x-ray examination of a patient without requiring removal of the electrodes or significantly impairing the x-ray image. For example, U.S. Pat. No. 5,265,579 issued to Ferrari discloses an x-ray transparent monitoring electrode and method for making that electrode. The electrode is used for continuous EKG monitoring. See column 1, line 55; column 2, line 8. A thin coating (a few microns in thickness; note that 1 mil=0.001 inches=0.0254 mm=25.4 microns) of silver—silver chloride 17a, 18a is applied, by silk screening, to a sheet of conductive carbon or graphite-filled polymer film that forms the x-ray translucent electrodes 17, 18. See column 3, line 67 to column 4, line 22. The x-ray translucent leads 24 have a tow of carbon fibers whose stripped ends are attached to the electrode using pressure-sensitive tape. See column 5, lines 51–54. The stripped ends are sandwiched between two portions of the tape. See column 7, lines 20–22. FIG. 2 of the patent illustrates that the stripped ends are fanned for attachment. A metallic coating such as nickel is applied to the carbon fibers. See column 6, lines 1–2.

B. Stimulating Electrodes

Stimulating electrodes emit electrical pulses for transcutaneous electrical devices, such as transcutaneous electrical nerve stimulation (TENS), electrical muscle stimulation (EMS), neuromuscular stimulation (NMS), functional electrical stimulation (FES), as well as interferential and iontophoresis therapy. Like monitoring electrodes, medical stimulating electrodes are also used to treat diseases and injuries in humans. Unlike and in contrast to monitoring electrodes, however, stimulation electrodes generally require a larger skin surface contact in order to provide sufficient transcutaneous electrical current to effect a desired physiologic response.

Many devices are designed for lower-energy level stimulation applications alone, such as TENS, EMS, NMS, FES, and interferential and iontophoresis therapy. At least some stimulation electrodes are touted as combination electrodes, which can also function as high-energy level defibrillation electrodes. U.S. Pat. No. 5,824,033 issued to Ferrari and was assigned to Ludlow Corporation. The patent discloses a disposable, multifunction (stimulating or defibrillating), x-ray transmissive electrode capable of conducting energy sufficient for defibrillation and which has improved current density distribution between the electrode and the skin of the patient. See column 2, lines 7–13, of the '033 patent. Ferrari notes that monitoring electrodes are incapable of conducting and distributing the high levels of energy required in transcutaneous stimulation and defibrillation electrodes; thus, an important distinction exists between high-energy stimulating or defibrillating electrodes and lower-energy stimulating or monitoring electrodes. See column 1, lines 29–32.

The disclosed electrode 10 includes an electrically conductive metal—metal chloride (e.g., silver—silver chloride) coating 23 applied to one side of a sheet electrode member 21. See column 3, lines 31–41. Ferrari teaches that the sheet electrode as coated with the electrically conductive metal—metal chloride is not alone capable of transmitting and distributing the high levels of energy encountered in defibrillation over the entire surface of the electrode member. See column 4, line 66 to column 5, line 4. Thus, a current distributing mat 27 is required and is adhered to the opposite side of the sheet electrode member.

The electrode member is a thin, flexible sheet of electrically conductive polymer film having a thickness of two to four mils (0.05 to 0.10 mm). The metal—metal chloride ink is applied in a layer or layers, by silk screening, and is preferably less than ten microns in thickness. See column 4, lines 17–30. The ink may be up to 1 mil (0.0254 mm) thick. The silk screen technique of applying the ink coating facilitates the application of multiple layers having different shapes and edge configurations to achieve a tiered effect. See column 10, lines 10–23.

The outer perimeter of the metal—metal chloride coating is spaced inward from the perimeter of the electrode member and outward from the perimeter of the mat. The metal—metal chloride coating is preferable formed in two layers 23', 23", each a few microns in thickness. In addition, the layers are serrated or undulated at their outer perimeter. See column 6, lines 12–45.

The electrical conductors 35 are multi-strand metal wires in which the unsheathed end portions 35a are strands that are spread out and fanned as shown in FIGS. 1 and 3 of the patent. The fanned ends are bonded to the surface of the mat by pressing them against the mat and folding the mat over the ends. Specifically, the wires are metallized carbon fiber tows with a metal (e.g., nickel or copper) coating. See column 6, line 46 to column 7, line 40.

C. Defibrillation Electrodes

In a malady called "fibrillation," the normal contractions of a muscle are replaced by rapid, irregular twitchings of muscular fibers (or fibrils). Fibrillation commonly occurs in the atria or ventricles of the heart muscle; the normal, rhythmical contractions of the heart are replaced by rapid, irregular twitchings of the muscular heart wall. A remedy for fibrillation is called "defibrillation," a procedure which applies an electric shock to arrest the fibrillation of the cardiac muscle (atrial or ventricular) and restore the normal heart rhythm.

Defibrillation electrodes must be capable of conducting the high-energy level required for defibrillation, up to 360 Joules or more. Defibrillation electrodes must also distribute the energy over a relatively large area of the epidermis of the patient to achieve adequate current density distribution within the atria or ventricles. These characteristics are sufficiently important that governmental regulatory agencies and medical industry groups have established standards for defibrillation electrodes. In particular, the American National Standards Institute (ANSI) standards for defibrillation electrodes have been published by the Association for the Advancement of Medical Instrumentation (AAMI). The ANSI standards for the size of defibrillation electrodes recommend, for example, that the minimum active area of individual, self-adhesive electrodes used for adult defibrillation and pacing shall be at least 50 $cm^2$ and that the total area of the two electrodes shall be at least 150 $cm^2$.

Many of the stimulating electrodes that have been disclosed do not comply with all of the defibrillation standards. The specification for defibrillation recovery characteristics, which describes certain time-related, electrical dissipation properties of the electrode following repeated electrical shocks of defibrillation currents, is especially difficult for many electrodes to meet. The use of non-compliant electrodes would invite the possibility of an inordinate, life-threatening delay following defibrillation. This restriction severely limits the usefulness of such electrodes in a critical care environment. Accordingly, many of these products bear a caution label that they are not to be used where defibrillation is a possibility.

U.S. Pat. No. 4,852,571 issued to Gadsby et al. addresses some of the shortcomings of these electrodes. The '571 patent discloses a disposable electrode which passes the electrical defibrillation requirements as specified by AAMI. The '571 design requires two separate layers of conductive inks, however, comprising a "discontinuous layer" of silver/silver chloride ink over a layer of carbon ink, which must be applied in two separate manufacturing steps. Avoidance of this dual-step ink-application requirement, which decreases process control, is desirable.

U.S. Pat. No. 5,352,315 was issued to Carrier et al. and was assigned to Ludlow Corporation. The '315 patent is directed to a biomedical electrode, suitable for defibrillation, that uses a conductive ink 7, 8 to provide varying impedances and at the same time is inexpensively produced and disposable as well. The conductive ink layer or layers may be of the silver and silver chloride type and may be applied by screen printing. The disclosed embodiments provide for the ink blends and ink amounts (i.e., ink thickness and ink pattern) to be varied so that the thickness and pattern provide a particular impedance value suited for the intended placement of the electrode at a particular body site.

The variation in impedance is preferably achieved by varying the ink surface coverage of the electrode. See column 8, lines 47–49. More specifically, the ink surface coverage of the backing material to which the ink is applied is between about 7% and 90% and, preferably, between about 14% and 28%. See column 6, lines 16–23. The thickness of the ink layer is generally in the range of 0.1 to 0.8 mils (0.00254 to 0.0203 mm). See column 6, lines 46–49.

In summary, the known defibrillation electrodes suffer from several shortcomings. Many of the electrodes, especially those incorporating costly snap connectors or bilayered inks which require dual-step ink application, are undesirably expensive to manufacture. Other known defibrillation electrodes have long defibrillation recovery times, impairing their ability to reliably function promptly after transmission of a defibrillation pulse through the electrode. Still other electrodes fail to compensate for impedance variances. Problems have been encountered with prior art defibrillation electrodes, particularly after application of repeated high-level defibrillation or cardiac pacing pulses, with irritation and burning of the patient's skin due to high current density around the perimeter of electrodes. It also remains a problem to improve the x-ray transparency of defibrillation electrodes.

To overcome the shortcomings of known defibrillation and pacing electrodes, a new disposable medical electrode intended for high-energy defibrillation and pacing with energy dispersion characteristics is provided. An object of the present invention is to provide a safe defibrillation electrode or set of electrodes which can compensate for impedance variances and can be economically manufactured, preferably in a continuous, automated process. A related object is to provide an improved electrode that features control of current density. Another object is to provide an electrode capable of conducting energy sufficient for defibrillation, and which has improved current density distribution between the electrode and the skin surface of the patient to efficiently deliver the energy without burning the patient's skin.

Yet another object is to provide an electrode that has an extremely low profile: when applied to the patient, the electrode lies substantially flat along the plane of the skin. A related object of the invention is to eliminate the rigid snap-type connector of the prior art and to create a medical electrode that is flexible over its entire area and thus more comfortable. All portions of the electrode are yielding and may conform to the patient's skin. The electrode offers no points of pressure when compressed against the skin by clothing or a mattress.

Another object of the invention is to create a medical electrode that may be left in place during radiographic procedures. Because the dense portions of the snap-type connector have been eliminated, the electrode of the present invention offers virtually no attenuation to x-rays and the small amount of attenuation that is produced is extremely uniform over the electrode surface. The electrode is substantially x-ray transparent.

SUMMARY OF THE INVENTION

To achieve these and other objects, and in view of its purposes, the present invention provides a disposable medical electrode that delivers high-energy defibrillation or pacing stimulation and has energy dispersion characteristics. The electrode includes an electrically conductive, carbon-filled polymer electrode member with a top face and a bottom face. A fanned wire contacts the top face of the electrode member for delivering energy to and transmitting energy from the electrode. An electrically conductive, skin-compatible hydrogel is disposed on at least a major portion of the bottom face of the electrode member. An electrically conductive metal/metal chloride ink coating underlies at least a major portion of the hydrogel on the bottom face of the electrode member. The ink coating has (a) a center with a first amount of ink, (b) an inner edge defining the terminus of the center and a step at which the ink content of the ink coating drops from the first amount of ink to a lesser second amount of ink, (c) an outer edge defining the terminus of the ink, and (d) a predetermined gradient disposed between the inner edge at which the ink coating has the second amount of ink, and the outer edge at which the ink is substantially absent. Finally, the electrode includes a removable release carrier sheet underlying and covering the hydrogel and the electrically conductive ink coating before use of the electrode.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
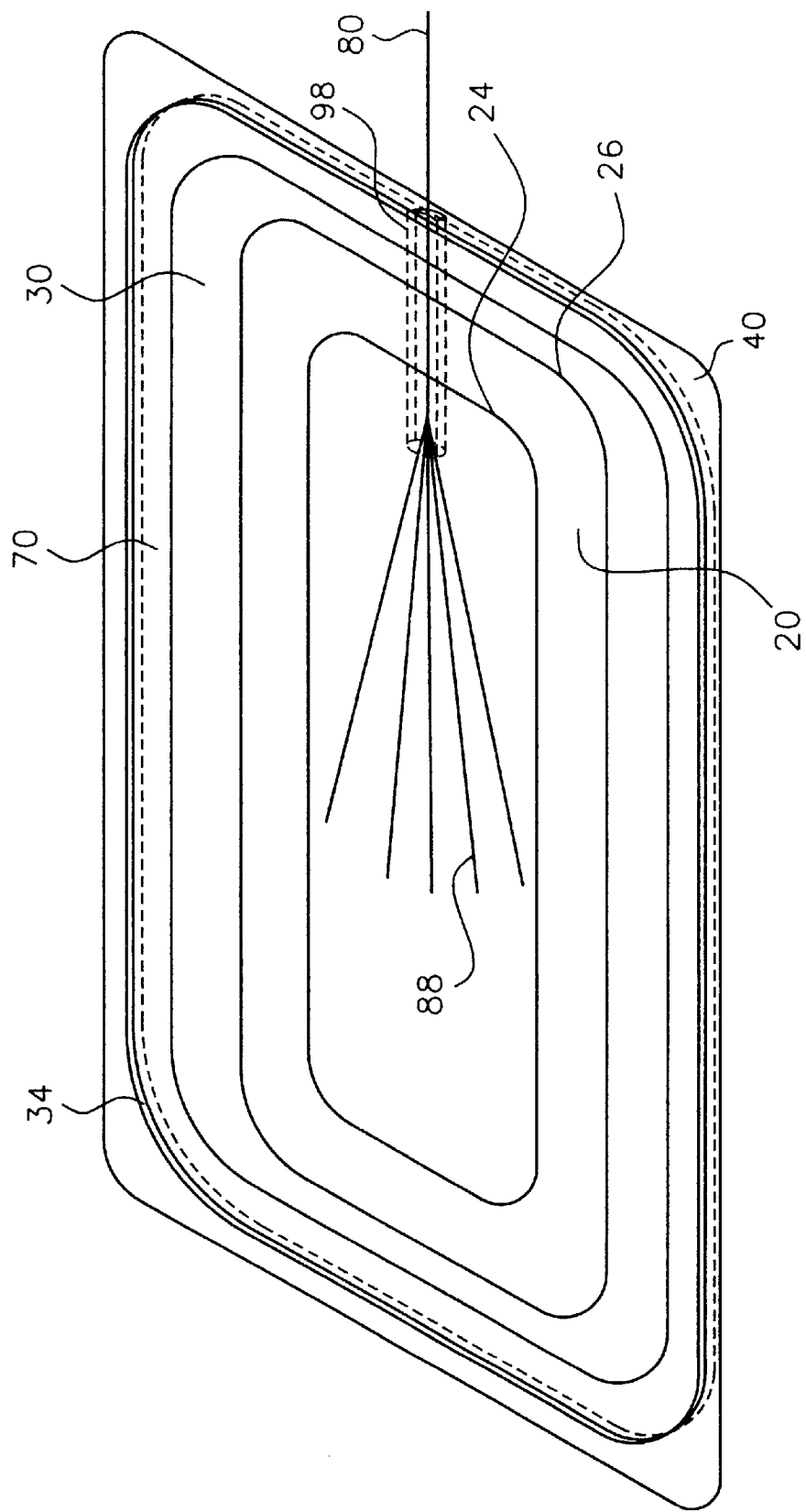
FIG. 1 is a perspective view illustrating the components of the medical defibrillation electrode according to a first embodiment of the present invention.

Referring now to the drawing, wherein like reference numbers refer to like elements throughout, the various embodiments of the present invention will be explained in detail following a detailed discussion of a conventional defibrillation electrode construction.

A. Conventional Defibrillation Electrode Construction

Figure 5A:
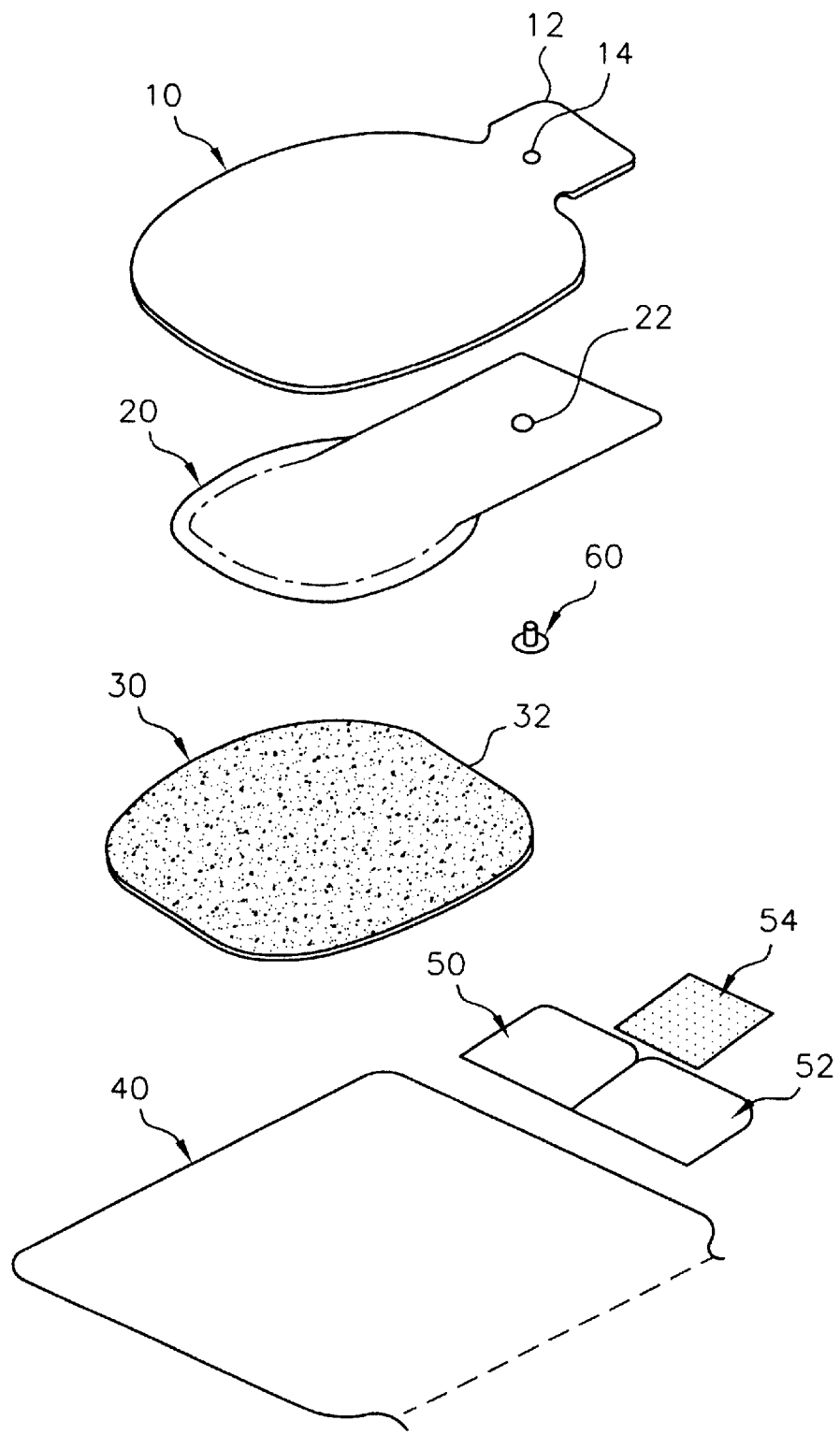
FIG. 5A is a perspective view, with components separated, of a conventional defibrillation electrode construction.

FIG. 5A shows, with components separated, a perspective view of a conventional defibrillation electrode construction. In general, the electrode comprises a sheet electrode member 10 of electrically conductive, carbon-filled polymer; an electrically conductive metal/metal chloride coating 20 (and preferably a silver/silver chloride coating) on at least a major portion of the lower side of the electrode member 10; and a pad of electrically conductive gel 30 underlying the metal/metal chloride coating 20 on the lower side of the electrode member 10. A removable release carrier sheet 40, for example of silicone-coated polyethylene terephthalate (PET), underlies the gel pad 30 and covers the latter before use. The electrode is configured to be x-ray transparent and capable of conducting electrical energy at levels sufficient for defibrillation. The phrase "x-ray transparent" is defined as the quality of being at least substantially invisible at x-ray irradiation levels used in routine x-rays of a patient's chest.

The electrode member 10 is formed of a thin, flexible sheet of electrically conductive polymer film such as graphite-filled polyvinyl chloride film preferably having a thickness of the order of two to four mils (0.05 to 0.10 mm). An example of carbon-filled polymer which can be used is thin, carbon-filled polyvinylchloride (PVC) available from Burkhardt/Freeman, Holyoke, Mass., under the trademark "Conducton." The electrode member 10 has a tab portion 12 with an aperture 14.

The electrode member 10 has a surface area dimensioned to distribute energy over an area of the patient's epidermis to achieve proper current density distribution within the ventricles of the patient's heart. The ANSI standards for the size of defibrillation electrodes published by AAMI recommend that the minimum active area of individual, self-adhesive electrodes used for adult defibrillation and pacing shall be at least 50 cm$^2$ and that the total area of two electrodes used in defibrillation shall be at least 150 cm$^2$. The electrode member 10 has an area of at least 50 cm$^2$ and preferably about 80 cm$^2$ or more so that a pair of the electrodes used for defibrillation can be of the same size.

The coating 20 of metal/metal chloride is applied in a layer or layers to the lower face of the electrode member 10 by silk screening or by flexographic printing. A carbon-filled PVC material with silver/silver chloride coating on the underside suitable for use as an electrode member is available from Prime Label And Screen, Inc., New Berlin, Wis. Alternatively, the metal/metal chloride coating 20 can comprise a single layer, chloride-coated metallic foil coated with a conductive acrylic adhesive. The metallic foil may comprise silver, tin, copper, nickel, gold, aluminum, platinum, chromium, cadmium, palladium, zinc, antimony, or indium covered with an adhesive such as the Arclad 8001 bonding tape or Arclad EC2 adhesive. An aperture 22 is provided in the coating 20 and positioned to align with the aperture 14 in the electrode member 10.

An electrolytic gel pad 30 underlies the metal/metal chloride coating 20 on the lower surface of the electrode member 10. The gel pad 30 is preferably a skin-compatible hydrogel having good ability to retain moisture content and adhesive tack. The gel pad 30 is of a type that adhesively connects the electrode to the patient's skin. The gel may comprise, for example, a hydrogel marketed by Ludlow Technical Products (a division of Tyco International Corporation) under the trademark "Procam," product number GRG73P.

At the head 32 of the gel pad 30 are provided a pair of foam tabs 50, 52. One of the tabs 52 is covered with an adhesive 54. An energy conductor 60 such as a conductive post, stud, or rivet is conductively adhered to the electrode construction. The conductor 60 aligns with, and passes through, both the aperture 22 in the coating 20 and the aperture 14 in the electrode member 10. Such a conductor 60 permits cost-effective use of the electrode with certain defibrillators currently on the market. The conductor 60 may be made of a conductive metal (such as nickel-plated brass or stainless steel) or a conductive plastic. The conductive plastic may be ABS plastic resin, nylon 12, or Carillon polymer crystal resin manufactured by Shell Oil, loaded with 25–40% nickelized carbon fibers. After being molded into its shape, the conductive plastic may be silver-coated (by, e.g., electrolysis) to further enhance its conductivity.

Figure 5B:
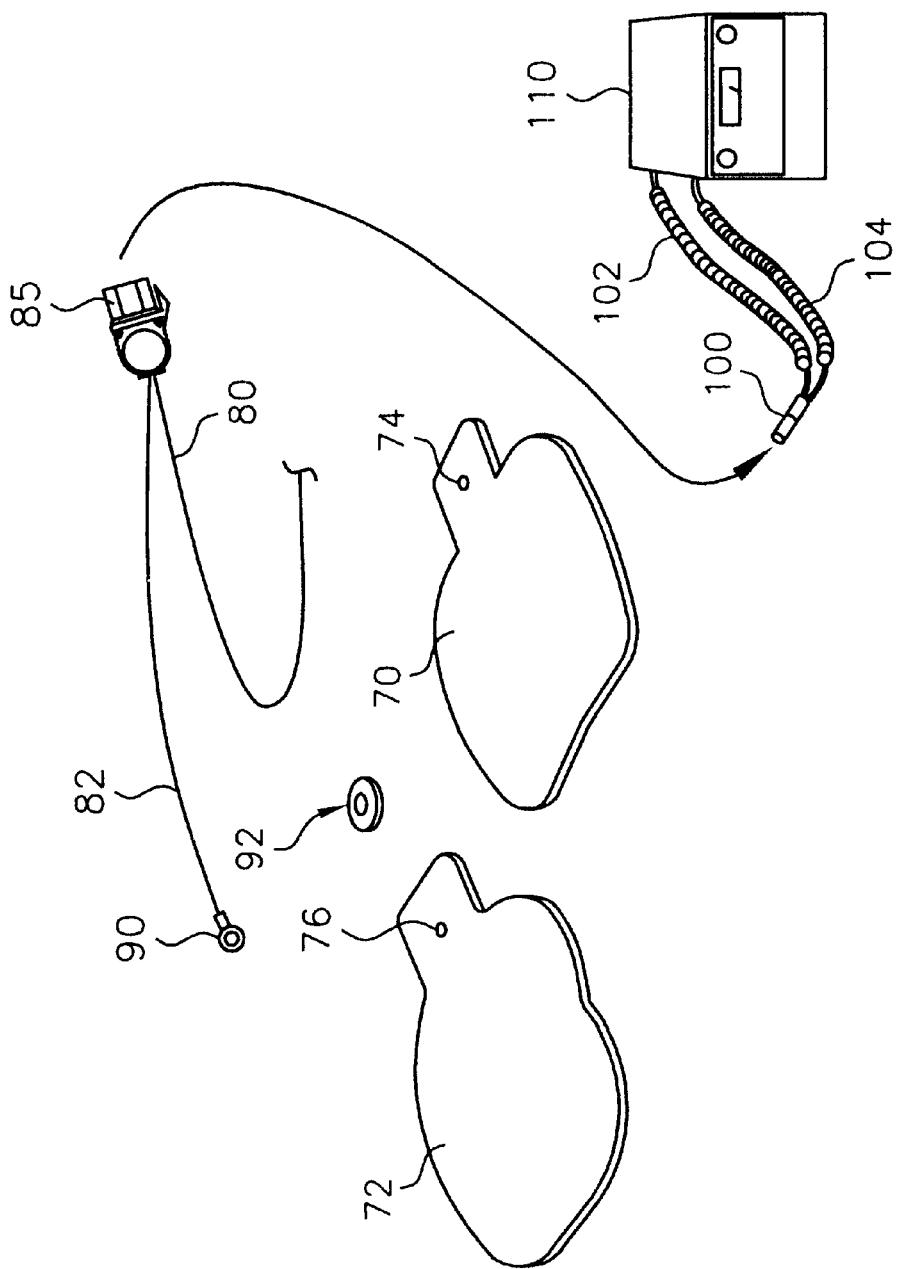
FIG. 5B is a perspective view of (a) the conventional cover sheets disposed on top of the two electrodes, each comprising the underlying components shown in FIG. 5A, that form a defibrillation pair of pad electrodes, and (b) the conventional connections between the electrodes and a defibrillator.

As shown in FIG. 5B, an oversized cover sheet 70 having an adhesive layer on its lower surface is secured to the top of the electrode member 10. The cover sheet 70 is x-ray transparent and made of electrically insulative foam such as 0.08 to 0.16 cm thick polyethylene (PE) foam. Shown in FIG. 5B are the two electrodes that form a defibrillation pair of pad electrodes, with cover sheet 70 forming the right pad and cover sheet 72 forming the left pad. The components underlying each of cover sheet 70, 72 are illustrated in FIG. 5A and discussed above. Cover sheet 70 has an aperture 74 and cover sheet 72 has an aperture 76. Each aperture 74, 76 aligns with both the aperture 22 in the coating 20 and the aperture 14 in the electrode member 10 respectively underlying the cover sheets 70, 72 and receives a respective conductor 60. Because the electrodes are x-ray transparent, they can be positioned on the patient at any of the customary positions used for defibrillation without adversely affecting x-rays of the patient's chest in areas underlying the electrodes.

As diagrammatically shown in FIG. 5B, the energy-delivery and energy-accepting electrodes, represented by their respective cover sheets 70, 72, are connected through conductors 80, 82 to a connector 85. The connector 85 engages a corresponding connector 100 having lead conductors 102, 104 which are connected, in turn, to a defibrillator 110. Conductors 80, 82 of connector 85 are mechanically and electrically connected to the respective energy-delivery and energy-accepting electrodes, through the conductor 60 of each electrode, using a conductive ring contact 90 and a foam ring 92.

Figure 5C:
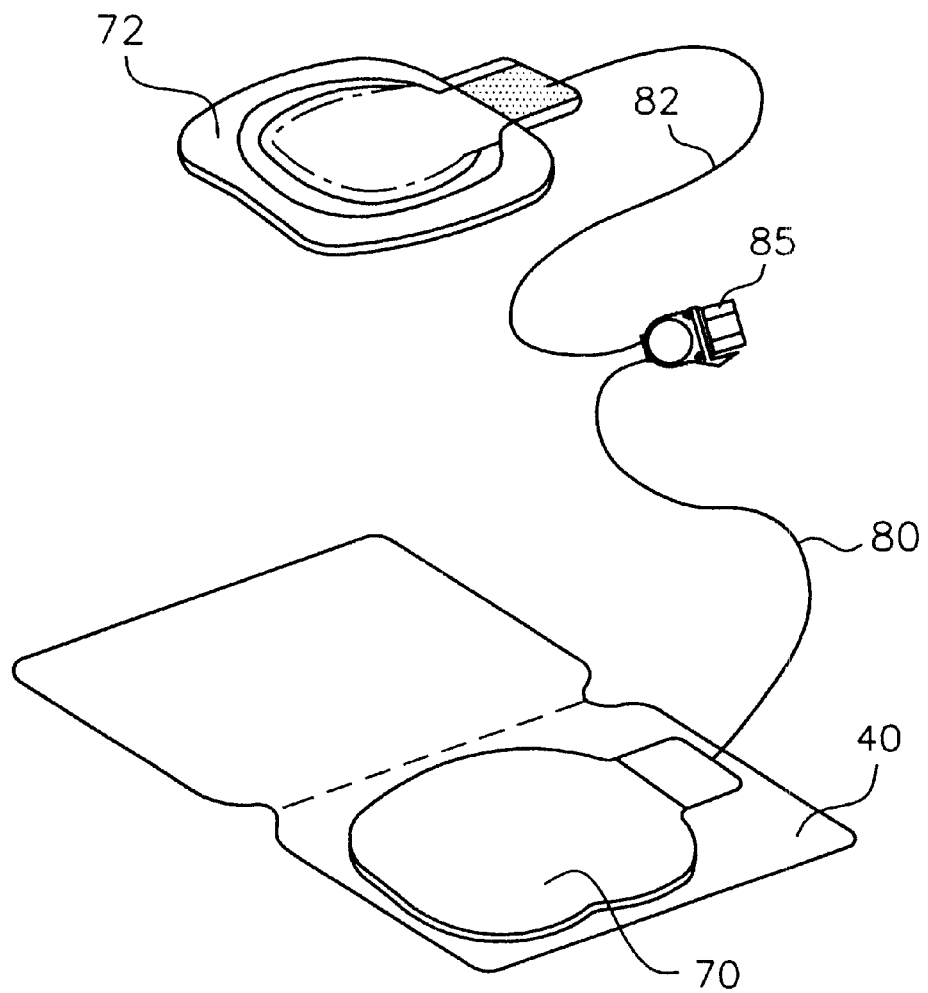
FIG. 5C illustrates the electrodes as engaged and ready to mate with the corresponding connector of the defibrillator.

FIG. 5C illustrates the electrodes and connector 85 as engaged and ready to mate with the corresponding connector 100 of the defibrillator 110. A top view of cover sheet 72 forming the left pad electrode is illustrated. A bottom view of cover sheet 70 forming the left pad electrode is illustrated.

The carbon-filled polymer electrode member 10 is conductive in the plane of the electrode and transverse to the plane of the electrode and the metal/metal chloride coating 20 on the under side of the electrode member 10 is also conductive in the plane of the coating and transverse to the plane of the coating. The carbon-filled polymer electrode member 10 has a surface resistance substantially higher than the surface resistance of the metal/metal chloride coating 20 and it has been found that the carbon-filled polymer electrode member 10 with a silver/silver chloride coating 20 is not alone capable of transmitting and distributing the high levels of energy encountered in defibrillation over the entire surface of the electrode member 10.

In addition, published literature indicates that, when a metal plate electrode having an electrolytic gel coating on its underside is placed on the skin and used to deliver current, the current density is very much higher under the perimeter of the electrode than under the center. A similar problem occurs at the energy-accepting electrode of a set of such defibrillation electrodes. Thus, a need exists for an electrode that distributes current more uniformly over the central portion of the electrode member.

The present invention meets that need, among its other advantages. The subject invention comprises a high-energy, disposable, medical, defibrillation electrode as described in detail below and as illustrated (in a first embodiment) in FIG. 1 and (in a second, preferred embodiment) in FIG. 4. The present invention also relates to a method of construction for a high-energy, disposable, medical, defibrillation electrode.

The invention provides a low-cost, disposable electrode suitable for high-energy stimulation (e.g., defibrillation, pacing, and the like) with an energy dispersion electrode pattern. When current passes through a surface electrode, the major portion of the current flows through the peripheral area of the electrode. In high-current applications, such as in external cardiac pacing and defibrillation via large surface electrodes, skin burns and pain can occur under the edges of the electrode where localized high-current density creates "hot spots." Thus, controlled energy dispersion and current distribution are important to high-current electrodes. In contrast, other electrodes such as biosignal monitoring electrodes have much smaller current densities and commensurately less need for controlled energy dispersion and current distribution.

Figure 4:
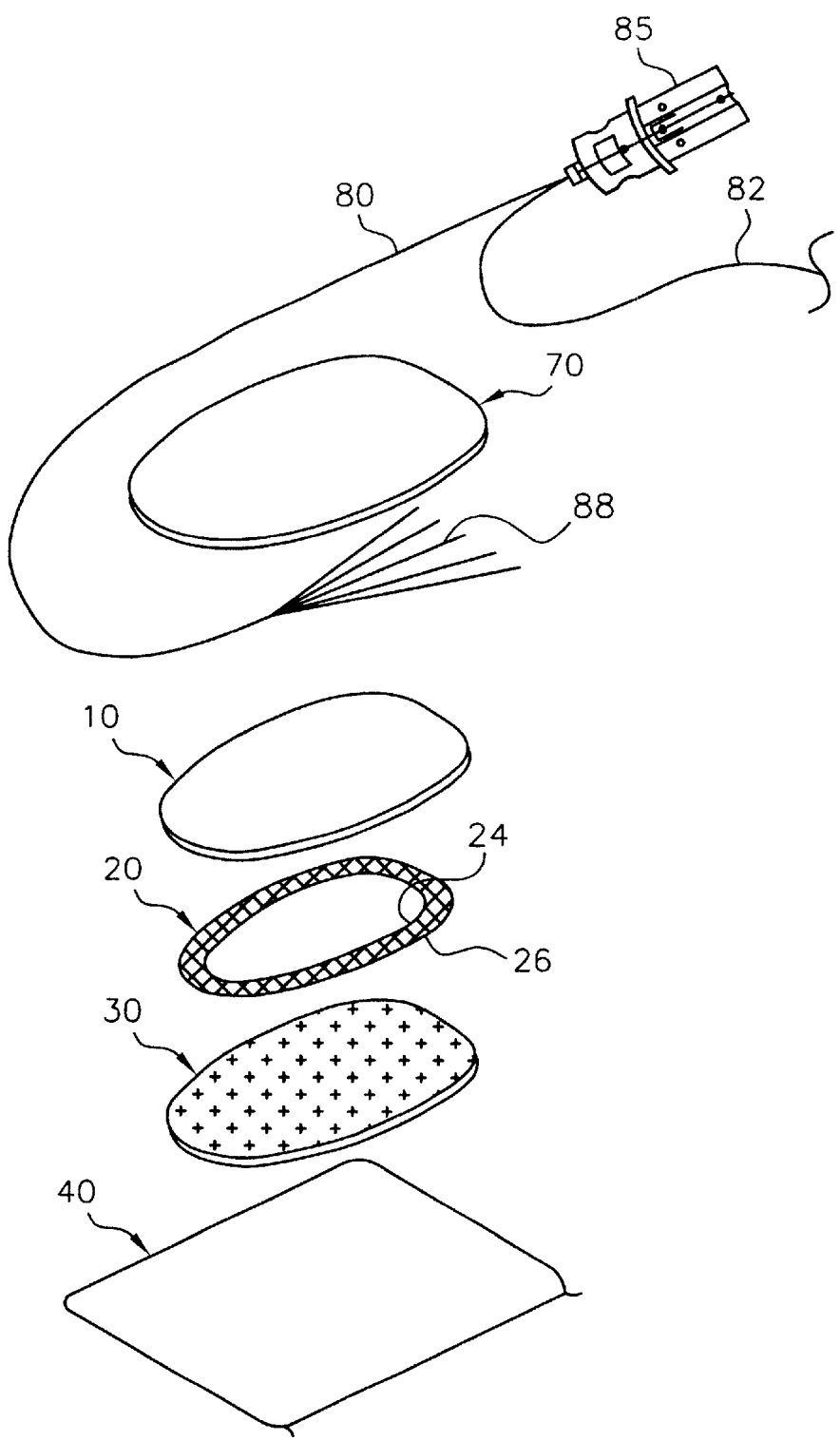
FIG. 4 is a perspective view illustrating the separated components of the medical defibrillation electrode according to a second, preferred embodiment of the present invention.

There are two, separate features of the invention that, both alone and in combination, help the defibrillation electrode of the subject invention achieve its advantages. The first feature involves the silver ink pattern used in the electrode structure to achieve energy dispersion. The second feature focuses on the attachment of an external lead or wire to the electrode body. Both features are illustrated in FIGS. 1 and 4.

B. First Embodiment of the Present Invention

As illustrated in FIG. 1, the electrode construction according to the present invention has a release carrier sheet 40. The release carrier sheet 40 may be made, for example, of silicone-coated PET. Although not required, a rectangular shape is suitable for the release carrier sheet 40. If rectangular as illustrated, dimensions such as a length of about 140 mm and a width of about 82 mm are suitable.

An oval-shaped foam barrier 34, having a substantially constant width of about 5 mm and a thickness of about 1 mm, is disposed on, and adjacent the edges of, the release carrier sheet 40. The foam barrier 34 defines a central opening approximately 65 mm wide and 122 mm long, in which is disposed and retained the gel pad 30. An adhesive may be provided on the patient-facing side of the foam barrier 34 to releasably affix the electrode to the skin of the patient.

The cover sheet 70, a continuous foam backing sheet without any openings and having a thickness of about 1 mm, extends to the outer dimensions of the foam barrier 34. Thus, the cover sheet 70 and the foam barrier 34 form a single peripheral edge for the electrode once the release carrier sheet 40 is removed. Affixed to the underside of the cover sheet 70 is an electrode member 10 (not illustrated in FIG. 1; see FIG. 5A). Electrode member 10 is formed of a thin, flexible sheet of electrically conductive polymer film such as graphite-filled polyvinyl chloride film preferably having a thickness of the order of two to four mils (0.05 to 0.10 mm).

A pad of electrically conductive gel 30 is retained within the boundaries of the foam barrier 34. Thus, gel 30 may be approximately 65 mm wide and 122 mm long. Over the electrically conductive gel 30 is applied a conductive metal/metal chloride coating 20 (and preferably a silver/silver chloride ink coating). The characteristics of the coating 20 are described more fully below. The release carrier sheet 40 covers and protects the gel pad 30 and the coating 20 before use.

The conductor 80, which delivers signals to and from the connector 85 (see FIGS. 5B and 5C), engages the electrode. The conductor 80 terminates in a fanned wire 88 in direct contact with the back of the carbon-vinyl film electrode member 10. The fanned wire 88 is kept in contact with the electrode member by sandwiching it with the adhesive-coated foam cover sheet 70 which is adhered to the back of the electrode member 10.

1. Ink Pattern

The pattern of the conductive silver/silver chloride ink coating 20 differs from previously disclosed technology (e.g., U.S. Pat. No. 5,824,033 and attached FIG. 5A) in several ways. First, at least the majority of the coating 20 is considerably thicker by a factor of six in order to enable the electrode to meet certain pacing requirements which the prior devices are unable to meet. The ink in conventional products is about ⅓ mil (0.0085 mm) thick; the substantially uniform thickness of the ink forming at least the central portion of the coating 20 is about 2 mils (0.058 mm) in the construction of the present invention.

Figure 2:
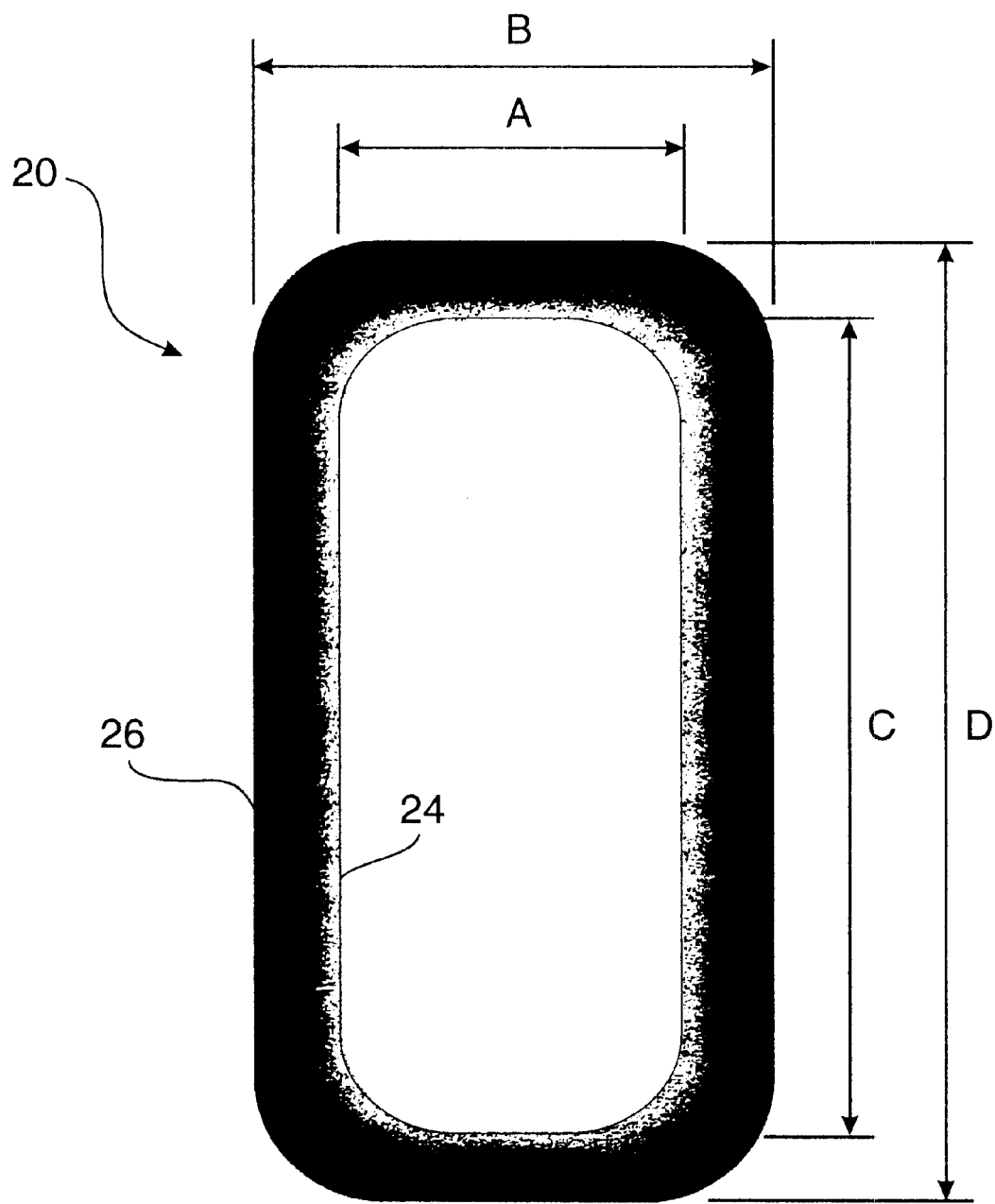
FIG. 2 illustrates the pattern of the conductive silver/silver chloride ink coating component, highlighting the ink gradient, of the medical defibrillation electrode shown in FIG. 1.

Another difference lies in the pattern of ink that is applied, termed a step-plus-gradient pattern. As shown in FIG. 2, the center of the pattern is substantially 100% ink and has a thickness of about 2 mils (0.058 mm). Both the composition and thickness of the ink are substantially constant in this center area. The center of the pattern is defined by the oval of approximate dimensions 1.60 inches or 40.6 mm (illustrated by line "A" in FIG. 2) by 3.855 inches or 97.9 mm (illustrated by line "C" in FIG. 2). The center oval of ink is also defined or bounded by the inner edge 24 of the ink coating 20.

At the inner edge 24 of the ink coating 20, a step or sudden change occurs in the ink composition. Specifically, the ink composition drops from substantially 100% ink to a specified percentage (e.g., 40% ink and 60% void) at precisely the inner edge 24 (i.e., with minimal change in distance). A gradient begins at the inner edge 24 of the center oval and extends to the outer edge 26 of the ink coating 20. The outer edge 26 of coating 20 is defined by the oval of approximate dimensions 2.10 inches or 53.3 mm (illustrated by line "B" in FIG. 2) by 4.355 inches or 110.6 mm (illustrated by line "D" in FIG. 2).

By "gradient" is meant a gradual and continuous decrease in the concentration of ink from the inner edge 24 to the outer edge 26. No steps in ink concentration occur in the region defined by the edges 24, 26. Rather, the ink composition continuously varies from the specified percentage (e.g., 40% ink and 60% void) at the inner edge 24 to zero at the peripheral outer edge 26 of the coating 20. The specified percentage and the gradient itself are predetermined in that both are reasonably predictable, as opposed to random, depending upon the performance characteristics of the defibrillation electrode ultimately desired.

Figure 3:
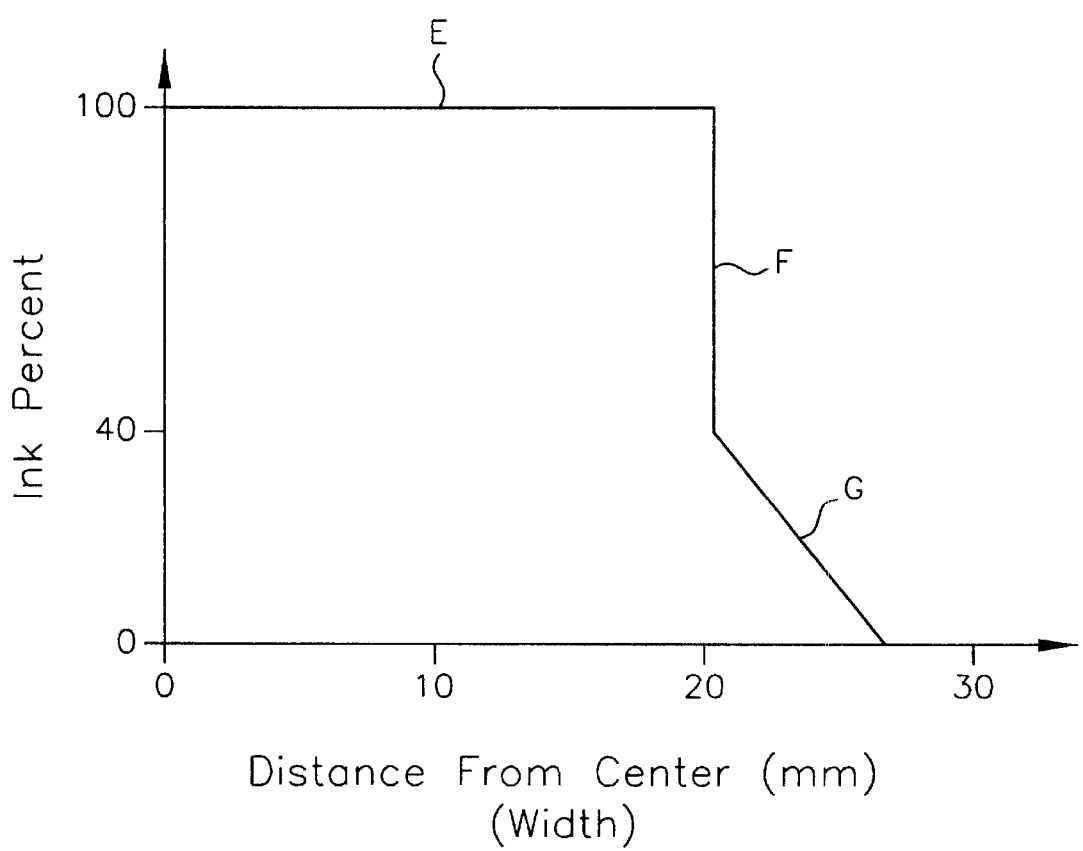
FIG. 3 is a graphical representation of the ink pattern illustrated in FIG. 2.

FIG. 3 is a graphical representation of the ink pattern illustrated in FIG. 2. The graph relates the ink composition, of the pattern that forms the coating 20 in the example used to illustrate the present invention, to the distance (width) from the center of the electrode. The graph depicts the substantially 100% ink composition in the center of the pattern as line "E." At precisely the inner edge 24, which is 20.3 mm from the center of the electrode, the composition drops to 40% ink and 60% void. These are the percentages specified in this example; the percentages might vary, of course, according to the application. The graph of FIG. 3 depicts this step (drop) in the amount of ink at the inner edge 24 as line "F." Finally, the gradient between the inner edge 24 and the outer edge 26 (which is 26.7 mm from the center of the electrode) of the ink coating 20 is depicted as line "G."

The step-plus-gradient pattern is formed using a dot pattern of ink that is applied with a silk screen (e.g., 137 mesh). Contrast the step-plus-gradient pattern of the present invention with the two layers of ink that are applied in the device disclosed in U.S. Pat. No. 4,852,571 (discussed above). The advantageous step-plus-gradient pattern of the present invention enables thicker deposits of ink to be applied while still providing a variation of impedance from the center to the edge of the coating 20.

2. Lead Attachment

The manner of connecting the defibrillation electrode of the present invention to the conductor 80 (which, in turn, is connected through the connector 85 to the defibrillator 110) is also of significance, and contributes to the overall effectiveness of the electrode. As shown in FIG. 1, the conductor 80 terminates in a significant length (greater than one inch or 25.4 mm and preferably about 2.75 inches or 70 mm) of spread out or fanned wire 88 placed in direct contact with the back of the carbon-vinyl film electrode member 10. Highly conductive, metal coated, carbon fibers such as copper-nickel coated carbon fibers are suitable to form the fanned wire 88. The fanned wire 88 is kept in contact with the electrode member by sandwiching it with the adhesive-coated foam cover sheet 70 which is adhered to the back of the electrode member 10.

The fanned wire 88 is provided to conduct current to or from the electrode member 10. In some applications, it is desirable that the fanned wire 88 be x-ray transparent. Such an x-ray transparent fanned wire 88 is preferably formed of metallized carbon fiber tows with an insulating sheath 98 formed of an x-ray transparent material. The carbon fiber tows are preferably of a size having between 3,000 to 12,000 fibers and metal plated with a metal coating that is about 20% to 50% by weight of the metal plated carbon fiber tow. The higher weight plating on the larger size tows provides improved current carrying capacity for repeated defibrillation pulses. Standard carbon fiber tows are made from a polyacrylonitrile precursor, are referred to as pan base carbon fiber, and are commercially available from Amoco Performance Products, Inc. of Atlanta, Ga.

In electrode applications where x-ray transparency of the conductors is not required, the fanned wire 88 can be formed of metal. Preferably, the metal fanned wire 88 is formed of multi-strand conductors which can be spread out to increase the contact area between the fanned wire 88 and the electrode member 10. When metal fanned wire 88 is used, the rest of the electrode remains x-ray transparent; only the metal fanned wire 88 appears on the x-rays.

The fanned wire 88 has the advantage of low mass relative to other conventional connection techniques. In combination with the manner of connection of the electrode to the defibrillator 110, the low mass minimizes the affect on the stability of the electrical connections caused by any patient motion (e.g., rolling over of the patient) or any tension on the fanned wire 88. Thus, the present design provides an inexpensive, disposable electrode capable of providing a consistent, highly accurate connection.

The low-cost method of connector attachment precludes the need for an energy-dispersion mat material as found in the device disclosed in U.S. Pat. No. 5,824,033 (discussed above). Other high-energy electrodes use solder, rivets, or a crimp to affix the electrode to the conductor. Still other electrodes use tabs to make the required electrical connection. All of these methods add significant cost to the electrode construction as well as being less radiolucent to x-rays.

Prior disposable biomedical electrodes ("snap connector electrodes") generally have a snap connector extending through the surface of the pad so that a snap stud presents itself on the upper surface of the electrode. Such a prior device is illustrated in FIGS. 5 and 5. Although snap connector electrodes have advantages over reusable needle or suction type electrodes, the snap connector must be of sufficient size to enable medical professionals to manipulate it and these electrodes are relatively expensive.

In addition, snap connectors constitute a source contributing to inconsistent performance of the electrode. Specifically, it has been found that, in use, the snap connector contributes significantly to the often erratic performance of the electrode. This connection provides considerable mass with respect to the remainder of electrode, such that patient movement results in alterations in the disposition of the electrode connector with respect to the skin of the patient. More specifically, any movement producing tension in the conductor (or lead wires) tends to pull the electrode connector away from the patient's skin. If the patient happens to roll over, the protruding nature of the snap connector forces the connector inwardly toward the skin and can cause discomfort. As a further problem, electrodes with projecting snap connectors do not lend themselves to stacking, and must be handled carefully during shipping and storage.

C. Second Embodiment of the Present Invention

Illustrated in FIG. 4 is a second, preferred embodiment of the electrode construction according to the present invention. The embodiment illustrated in FIG. 4 is similar in many respects to, although certain features are not shared with, the first embodiment illustrated in FIG. 1. With reference to FIG. 4, the electrode construction of the second embodiment has a release carrier sheet 40. Like the first embodiment, the release carrier sheet 40 may be made of silicone-coated PET and, although not required, have a rectangular shape. If rectangular as illustrated, dimensions such as a length of about 165 mm and a width of about 135 mm are suitable.

Unlike the first embodiment, the cover sheet 70 of the electrode construction of the second embodiment has a pear-shaped configuration. The cover sheet 70 is a continuous foam backing sheet without any openings and having a thickness of about 1 mm, a major axis of about 156 mm, and a minor axis of about 105 mm. Thus, the cover sheet 70 forms a single peripheral edge for the electrode once the release carrier sheet 40 is removed. An adhesive is provided on the patient-facing side of the cover sheet 70 to releasably affix the release carrier sheet 40 to the cover sheet 70 and, once the release carrier sheet 40 is removed, to releasably affix the electrode to the skin of the patient.

Affixed to the underside of the cover sheet 70 is an electrode member 10. Electrode member 10 is formed of a thin, flexible sheet of electrically conductive polymer film such as graphite-filled polyvinyl chloride film preferably having a thickness of the order of two to four mils (0.05 to 0.10 mm). Electrode member 10 has a pear-shaped configuration with a major axis of about 137 mm, and a minor axis of about 84 mm.

A conductive metal/metal chloride coating 20 (and preferably a silver/silver chloride ink coating) is disposed on the electrode member 10. The characteristics of the coating 20 are similar to those of the first embodiment and are described more fully below. A pad of electrically conductive gel 30 is disposed on the coating 20. The gel pad 30 may be approximately the same size and shape as the electrode member 10. The release carrier sheet 40 covers and protects the gel pad 30 and the coating 20 before use.

The conductor 80, which delivers signals to and from the connector 85, engages the electrode. The conductor 80 terminates in a fanned wire 88 in direct contact with the back of the carbon-vinyl film electrode member 10. The fanned wire 88 is kept in contact with the electrode member by sandwiching it with the adhesive-coated foam cover sheet 70 which is adhered to the back of the electrode member 10. Connector 85 also has a separate conductor 82 which engages the second electrode in the defibrillator electrode pair.

The pattern of the conductive silver/silver chloride ink coating 20 for the second embodiment is similar to that of the first embodiment. Specifically, the substantially uniform thickness of the ink forming at least the central portion of the coating 20 is about 2 mils (0.058 mm). The ink is applied in the same step-plus-gradient pattern. Thus, the center of the pattern is substantially 100% ink and has a thickness of about 2 mils (0.058 mm). Both the composition and thickness of the ink are substantially constant in this center area. The center of the pattern is defined by a pear shape with a major axis of about 105 mm and a minor axis of about 52 mm. The center oval of ink is also defined or bounded by the inner edge 24 of the ink coating 20.

At the inner edge 24 of the ink coating 20, a step or sudden change occurs in the ink composition. Specifically, the ink composition drops from substantially 100% ink to a specified percentage (e.g., 40% ink and 60% void) at precisely the inner edge 24 (i.e., with minimal change in distance). A gradient begins at the inner edge 24 of the center oval and extends to the outer edge 26 of the ink coating 20. The outer edge 26 of coating 20 is defined by a pear shape with a major axis of about 120 mm and a minor axis of about 68 mm.

By "gradient" is meant a gradual and continuous decrease in the concentration of ink from the inner edge 24 to the outer edge 26. No steps in ink concentration occur in the region defined by the edges 24, 26. Rather, the ink composition continuously varies from the specified percentage (e.g., 40% ink and 60% void) at the inner edge 24 to zero at the peripheral outer edge 26 of the coating 20. The specified percentage and the gradient itself are predetermined in that both are reasonably predictable, as opposed to random, depending upon the performance characteristics of the defibrillation electrode ultimately desired.

Figure 4A:
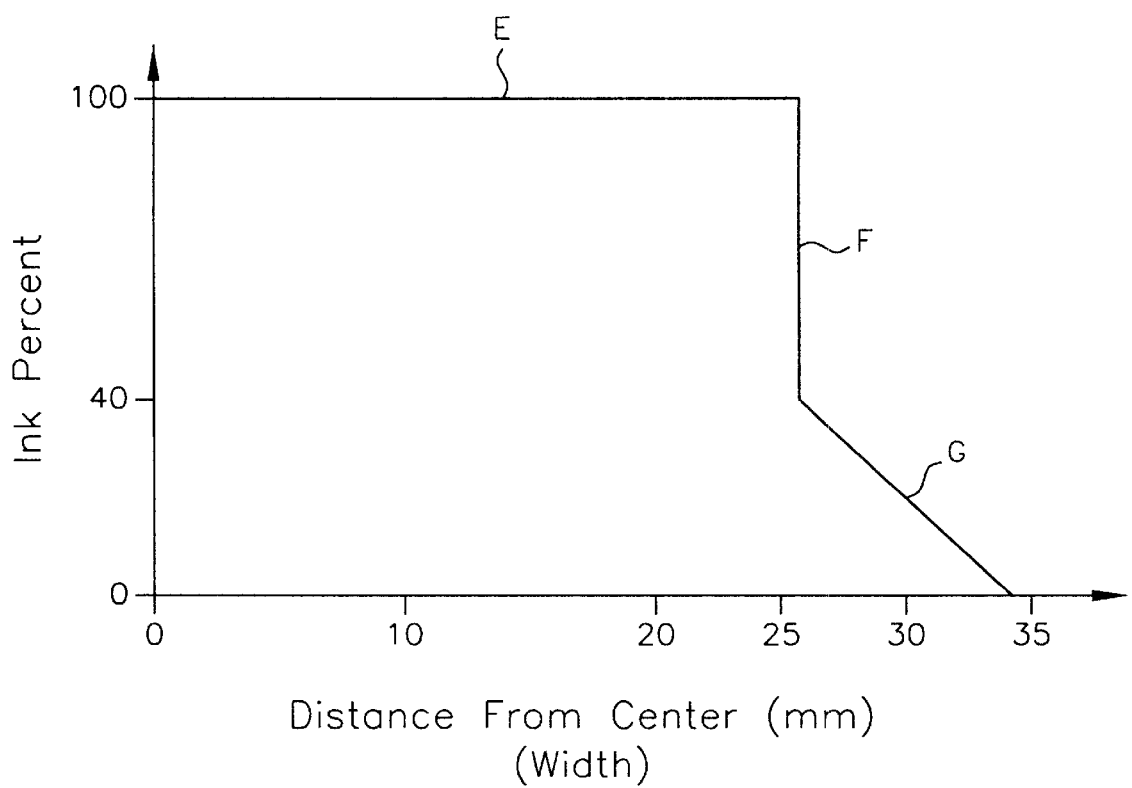
FIG. 4A is a graphical representation of the ink pattern illustrated in FIG. 4.

FIG. 4A is a graphical representation of the ink pattern illustrated in FIG. 4. The graph relates the ink composition, of the pattern that forms the coating 20 in the second embodiment, to the distance (width) from the center of the electrode. The graph depicts the substantially 100% ink composition in the center of the pattern as line "E." At precisely the inner edge 24, which is about 26 mm from the center of the electrode, the composition drops to 40% ink and 60% void. These are the percentages specified in this example; the percentages might vary, of course, according to the application. The graph of FIG. 4A depicts this step (drop) in the amount of ink at the inner edge 24 as line "F." Finally, the gradient between the inner edge 24 and the outer edge 26 (which is about 34 mm from the center of the electrode) of the ink coating 20 is depicted as line "G."

Other features of the second embodiment of the present invention are similar to corresponding features of the first embodiment. Specifically, the step-plus-gradient pattern is formed using a dot pattern of ink that is applied in the same way regardless of the embodiment. The manner of connecting the defibrillation electrode of the second embodiment of the present invention to the conductor 80 is also the same as for the first embodiment.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A disposable medical electrode for delivering high-energy defibrillation or pacing stimulation and having energy dispersion characteristics, the electrode comprising:

an electrode member having a top face and a bottom face;

an electrical connector in contact with the top face of the electrode member for delivering energy to and transmitting energy from the electrode;

an electrically conductive gel on at least a major portion of the bottom face of the electrode member; and an electrically conductive coating underlying at least a major portion of the gel on the bottom face of the electrode member and having:
  (a) a center with a first amount of conductor;
  (b) an inner edge defining the terminus of the center;
  (c) an outer edge defining the terminus of the coating at which the conductor is substantially absent; and
  (d) a predetermined gradient disposed between the inner edge and the outer edge.

2. The defibrillation electrode according to claim 1 wherein the electrically conductive coating further has a step at the inner edge defining the terminus of the center at which the conductor drops from the first amount of conductor to a second amount of conductor.

3. The defibrillation electrode according to claim 1 further comprising a removable release carrier sheet underlying and covering the gel and the electrically conductive coating before use of the electrode.

4. The defibrillation electrode according to claim 1 wherein the electrode member is an electrically conductive, carbon-filled polymer; the electrically conductive coating is metal/metal chloride; and the gel is a skin-compatible hydrogel.

5. The defibrillation electrode according to claim 4 wherein the electrically conductive coating is silver/silver chloride.

6. The defibrillation electrode according to claim 1 wherein the electrode member has an area of at least 50 cm$^2$.

7. The defibrillation electrode according to claim 1 further comprising a cover sheet having an underside to which the electrode member is affixed, whereby the electrical connector is sandwiched by and held between the cover sheet and the electrode member, and a removable release carrier sheet underlying and covering the gel and the electrically conductive coating before use of the electrode and having peripheral edges.

8. The defibrillation electrode according to claim 1 wherein the electrical connector comprises a fanned wire.

9. The defibrillation electrode according to claim 8 wherein the length of the fanned wire is at least 25 mm.

10. The defibrillation electrode according to claim 9 wherein the length of the fanned wire is about 70 mm.

11. The defibrillation electrode according to claim 8 wherein the fanned wire comprises conductive, metal coated, carbon fibers.

12. The defibrillation electrode according to claim 1 wherein the electrically conductive coating is an ink coating.

13. The defibrillation electrode according to claim 12 wherein the center of the ink coating has a substantially uniform thickness of about 0.05 mm.

14. A disposable medical electrode for delivering high-energy defibrillation or pacing stimulation and having energy dispersion characteristics, the electrode comprising:

an electrode member having a top face and a bottom face;

an electrical connector in contact with the top face of the electrode member for delivering energy to and transmitting energy from the electrode;

an electrically conductive gel on at least a major portion of the bottom face of the electrode member;

an electrically conductive coating underlying at least a major portion of the gel on the bottom face of the electrode member and having:
  (a) a center with a first amount of conductor,
  (b) an inner edge defining the terminus of the center and a step at which the conductor drops from the first amount of conductor to a second amount of conductor,
  (c) an outer edge defining the terminus of the coating and at which the conductor is substantially absent, and
  (d) a predetermined gradient disposed between the inner edge and the outer edge; and a removable release carrier sheet underlying and covering the gel and the electrically conductive coating before use of the electrode and having peripheral edges.

15. The defibrillation electrode according to claim 14 wherein the electrode member is an electrically conductive, carbon-filled polymer; the electrically conductive coating is metal/metal chloride; and the gel is a skin-compatible hydrogel.

16. The defibrillation electrode according to claim 15 wherein the electrically conductive coating is silver/silver chloride.

17. The defibrillation electrode according to claim 14 wherein the electrode member has an area of at least 50 cm$^2$.

18. The defibrillation electrode according to claim 14 further comprising a cover sheet having an underside to which the electrode member is affixed, whereby the electrical connector is sandwiched by and held between the cover sheet and the electrode member.

19. The defibrillation electrode according to claim 14 wherein the electrical connector comprises a fanned wire.

20. The defibrillation electrode according to claim 19 wherein the length of the fanned wire is at least 25 mm.

21. The defibrillation electrode according to claim 20 wherein the length of the fanned wire is about 70 mm.

22. The defibrillation electrode according to claim 19 wherein the fanned wire comprises conductive, metal-coated, carbon fibers.

23. The defibrillation electrode according to claim 14 wherein the electrically conductive coating is an ink coating.

24. The defibrillation electrode according to claim 23 wherein the center of the ink coating has a substantially uniform thickness of about 0.05 mm.

25. A disposable medical electrode for delivering high-energy defibrillation or pacing stimulation and having energy dispersion characteristics, the electrode comprising:

an electrically conductive, carbon-filled polymer electrode member having a top face and a bottom face;

a fanned wire in contact with the top face of the electrode member for delivering energy to and transmitting energy from the electrode;

an electrically conductive skin-compatible hydrogel on at least a major portion of the bottom face of the electrode member;

an electrically conductive metal/metal chloride ink coating underlying at least a major portion of the hydrogel on the bottom face of the electrode member and having:
  (a) a center with a first amount of ink,
  (b) an inner edge defining the terminus of the center and a step at which the ink content of the ink coating drops from the first amount of ink to a lesser second amount of ink,
  (c) an outer edge defining the terminus of the ink, and
  (d) a predetermined gradient disposed between the inner edge at which the ink coating has the second amount of ink, and the outer edge at which the ink is substantially absent; and a removable release carrier sheet underlying and covering the hydrogel and the electrically conductive ink coating before use of the electrode and having peripheral edges.

26. The defibrillation electrode according to claim 25 wherein the electrically conductive coating is silver/silver chloride.

27. The defibrillation electrode according to claim 25 wherein the electrode member has an area of at least 50 cm$^2$.

28. The defibrillation electrode according to claim 25 further comprising a cover sheet having an underside to which the electrode member is affixed, whereby the fanned wire is sandwiched by and held between the cover sheet and the electrode member.

29. The defibrillation electrode according to claim 25 wherein the length of the fanned wire is at least 25 mm.

30. The defibrillation electrode according to claim 29 wherein the length of the fanned wire is about 70 mm.

31. The defibrillation electrode according to claim 25 wherein the fanned wire comprises conductive, metal-coated, carbon fibers.

32. The defibrillation electrode according to claim 25 wherein the center of the ink coating has a substantially uniform thickness of about 0.05 mm.

33. The defibrillation electrode according to claim 25 wherein the first amount of ink is substantially 100% and the second amount of ink is about 40%.

* * * * *